(12) United States Patent
Korteling et al.

(10) Patent No.: US 6,497,703 B1
(45) Date of Patent: Dec. 24, 2002

(54) CRYOABLATION CATHETER FOR LONG LESION ABLATIONS

(75) Inventors: Bart-Jan Korteling, Mission Viejo, CA (US); Hendrikus Willem Wegereef, Peize (NL)

(73) Assignee: Biosense Webster, Diamond Bar, CA (US)

( * ) Notice: Subject to any disclaimer, the term of this patent is extended or adjusted under 35 U.S.C. 154(b) by 0 days.

(21) Appl. No.: 09/518,044

(22) Filed: Mar. 2, 2000

(51) Int. Cl.⁷ ............................................ A61B 18/02
(52) U.S. Cl. ......................................................... 606/23
(58) Field of Search .................................. 600/153–158; 606/20–26, 41, 47, 21

(56) References Cited

U.S. PATENT DOCUMENTS

| | | | |
|---|---|---|---|
| 3,125,906 A | | 3/1964 | Antiles et al. |
| 3,662,755 A | * | 5/1972 | Rautenbach et al. ........... 606/24 |
| 3,859,986 A | | 1/1975 | Okada et al. |
| 3,971,383 A | * | 7/1976 | van Gerven ................. 606/23 |
| 4,015,606 A | | 4/1977 | Mitchiner et al. |
| 5,078,713 A | | 1/1992 | Varney |
| 5,281,213 A | | 1/1994 | Milder et al. |
| 5,281,215 A | | 1/1994 | Milder |
| 5,324,286 A | * | 6/1994 | Fowle .......................... 606/23 |
| 5,423,807 A | | 6/1995 | Milder |
| 5,674,218 A | * | 10/1997 | Rubinsky et al. .............. 606/20 |
| 5,800,487 A | | 9/1998 | Mikus et al. |
| 5,807,391 A | | 9/1998 | Wijkamp |
| 5,906,612 A | | 5/1999 | Chinn |
| 5,916,213 A | * | 6/1999 | Haissaguerre et al. ......... 606/41 |
| 5,957,963 A | * | 9/1999 | Dobak et al. ................ 607/104 |
| 5,980,519 A | * | 11/1999 | Hahnen et al. ................ 606/49 |
| 6,151,901 A | * | 11/2000 | Dobak et al. ................. 62/51.2 |
| 6,241,722 B1 | * | 6/2001 | Dobak et al. .................. 606/23 |
| 6,280,439 B1 | * | 8/2001 | Martin et al. .................. 606/21 |

FOREIGN PATENT DOCUMENTS

| | | |
|---|---|---|
| EP | 0 407 229 | 1/1991 |
| GB | 2 094 936 A | 9/1982 |
| WO | WO 92/04872 | 4/1992 |
| WO | 94/18896 | 9/1994 |
| WO | 97/48451 | 12/1997 |
| WO | WO 99/27862 | 6/1999 |

\* cited by examiner

*Primary Examiner*—Linda C. M. Dvorak
*Assistant Examiner*—Henry M. Johnson, III
(74) *Attorney, Agent, or Firm*—George H. Gerstman; Seyfarth Shaw

(57) ABSTRACT

The present invention relates to a cryoablation catheter, comprising an outer tubular body with a closed distal end to form a fluid cooling chamber and an inner tubular member having a proximal end adapted to receive fluid suitable for cryoablation and a distal end coupled to a fluid expansion nozzle wherein the inner tubular member is movable in an axial direction to thereby change the position of the nozzle within the fluid cooling chamber.

8 Claims, 3 Drawing Sheets

CRYOABLATION CATHETER FOR LONG LESION ABLATIONS

BACKGROUND OF THE INVENTION

1. Field of the Invention

The present invention relates to a cryoablation catheter, and more particularly to a cryoablation catheter for creating long lesions.

2. Description of the Prior Art

Many medical procedures are performed using minimally invasive surgical techniques wherein one or more slender implements are inserted through one or more small incisions into a patient's body. With respect to ablation, the surgical implement may include a rigid or flexible structure having an ablation device at or near its distal end that is placed adjacent to the tissue to be ablated. Radio frequency energy, microwave energy, laser energy, extreme heat, and extreme cold may be provided by the ablation device to destroy the tissue.

With respect to cardiac procedures, a cardiac arrhythmia may be treated through selective ablation of cardiac tissue to eliminate the source of the arrhythmia. A popular minimally invasive procedure, radio frequency (RF) catheter ablation, includes a preliminary step of conventional electrophysiology mapping followed by the creation of one or more ablated regions (lesions) in the cardiac tissue using RF energy. Multiple lesions are frequently required because the effectiveness of each of the lesion sites can not be predetermined with exactness due to limitations of conventional mapping. Often, five lesions, and sometimes as many as twenty lesions may be required before a successful result is attained. Usually only one of the lesions is actually effective.

Deficiencies of radio frequency ablation devices and techniques have been overcome by ice mapping prior to creating lesions, as taught by U.S. Pat. Nos. 5,423,807; 5,281,213 and 5,281,215. However, even though combined cryogenic mapping and ablation devices permit greater certainty and less tissue damage than RF devices and techniques, both the cryogenic and the RF devices are configured for spot or roughly circular tissue ablation.

Spot tissue ablation is acceptable for certain procedures. However, other procedures can be more therapeutically effective if multiple spot lesions are made along a predetermined line, or a single elongate or linear lesion is created in a single ablative step. Radio frequency ablation devices are known to be able to create linear lesions by dragging the ablation tip along a line while the ablation electrode is energized.

SUMMARY OF THE INVENTION

The present invention provides a cryogenic ablation system including a cryoablation catheter which is particularly well suited for creating elongated lesions.

In accordance with one aspect of the present invention, there is provided a cryoablation catheter which includes an outer tubular member capable of insertion into the vessels of the body, a sealing cap disposed at the distal end of the outer tubular member for forming a cooling chamber at the distal end of the catheter, and an inner tubular member which is slidably disposed within the outer tubular member. A fluid expansion nozzle is disposed on the distal end of the inner tubular member. The cryoablation catheter also includes a control means coupled to the proximal end of the inner tubular member for moving the inner tubular member longitudinally within the outer tubular member to thereby change the position of the fluid expansion nozzle within the cooling chamber. Preferably the fluid expansion nozzle takes the form of a Joule-Thompson nozzle. By moving the nozzle longitudinally within the cooling chamber it is possible to create a continuous long lesion along the entire length of the movement of the nozzle.

In accordance with another aspect of the present invention, the inner tubular member is disposed coaxially within the outer tubular member so as to define a passageway between the tubular members. A cylindrical support member is disposed between the inner tubular member and the outer tubular member and includes at least one aperture which extends through the support member to permit expanded fluid to return through the passageway to the proximal end of the catheter for removal from the system, or in a closed system for reprocessing for further use.

In accordance with still another aspect of the present invention, the control means takes the form of a control knob which is connected to the proximal end of the inner tubular member for controlling movement of the inner tubular member longitudinally within the outer tubular member to thereby change the position of the fluid expansion nozzle relative to the distal end of the cooling chamber.

These and other objects of the present invention will become more apparent when considered in view of the following description of a preferred embodiment of the present invention.

BRIEF DESCRIPTION OF THE DRAWINGS

Further properties, advantages and measures according to the present invention will be explained in greater detail in the description of a preferred embodiment, with reference to the attached figures in which.

DESCRIPTION OF THE PREFERRED EMBODIMENT

Figure 1:
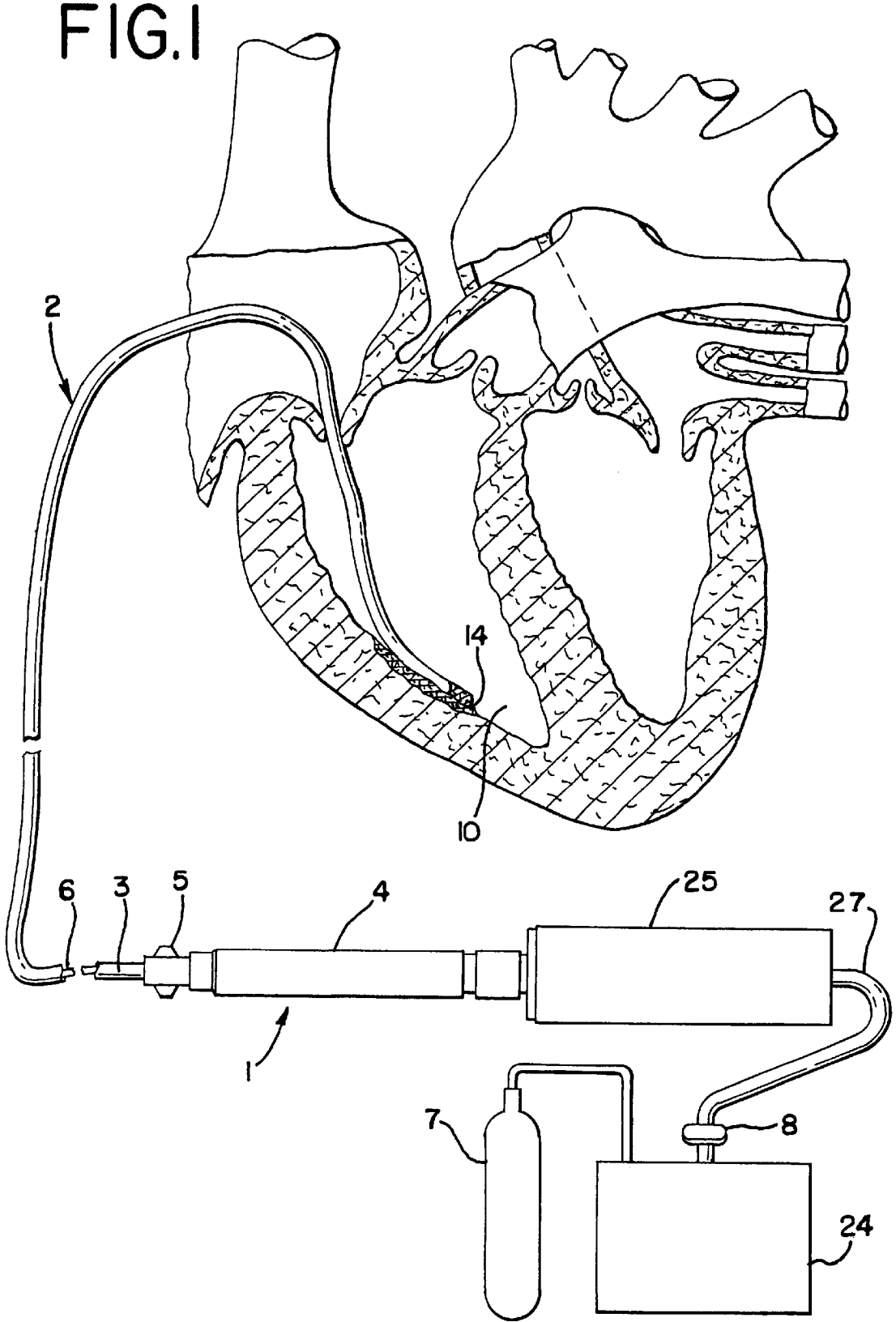
FIG. 1 is a schematic view of a system for cryoablation with a catheter according to the present invention placed within a human heart.

FIG. 1 a cryoablation catheter system 1 according to the present invention has been illustrated with a catheter 2. The catheter 2 comprises a basic body 3, an internal body 6, a connecting piece 4 and a handle 5. The handle 5 is connected with the internal body 6 and the connecting piece 4 with the basic body 3, whereby the handle 5 is movable in the axial direction of the catheter 2 in relation to the connecting piece 4 in such a way that the distal tip of the internal body 6, where the internal body 6 opens out into the lumen of the basic body 3, is movable in an axial direction with respect to the distal tip of the catheter 2.

The handle 5 is connected via a heat exchanger 25, a connecting tube 27 through a control unit 24 and a tap 8 with a gas cylinder 7, containing $N_2O$. By way of an alternative, or as an addition, also other substances than $N_2O$ may be used. Preferably, a fluid is used of which the cooling effect only occurs on expansion when it is ejected via the internal body 6 close to the distal end of the catheter 2 into the lumen of the basic body 3. This fluid will expand, as a result of which the cooling effect will be achieved. $N_2O$ meets this requirement with satisfactory results.

The embodiment of the tap 8 illustrated here is very basic. The tap 8 is part of, or constitutes the control means with which the flow of $N_2O$ through the internal body 6, and the pressure inside this internal body 6 are regulated. The pressure depends on the intended effect of the cryoablation at the distal tip of the catheter 2. In an embodiment of the present invention not illustrated here, the catheter 2 has been provided near to the distal end with measuring equipment, such as a thermocouple, which also forms part of the control means, in which case the tap 8 is activated on the basis of the measuring results obtained at the thermocouple. In that case the measurement of the temperature is set to a target value established in advance, in order to effect the required degree of cryoablation.

The tip at the distal end of the catheter 2 may also be provided with other measurement equipment to determine the position of the nozzle 12 for instance. Examples of such measuring equipment are marking rings which are recognizable when using imaging techniques like MRI or when using x-ray radiation. Equipment to determine whether the surrounding tissue also needs to be ablated may be included here as well.

In the situation illustrated schematically in FIG. 1, the distal end of the catheter 2 has been introduced into a chamber of the heart 10 and advanced to a position where tissue 14 is located which is suitable for ablation. It could however also concern here applications in a vein or at any other location. The only thing which is important, is that in the body cavity there is tissue, like the tissue 14 illustrated here, which qualifies for ablation.

Figure 2:
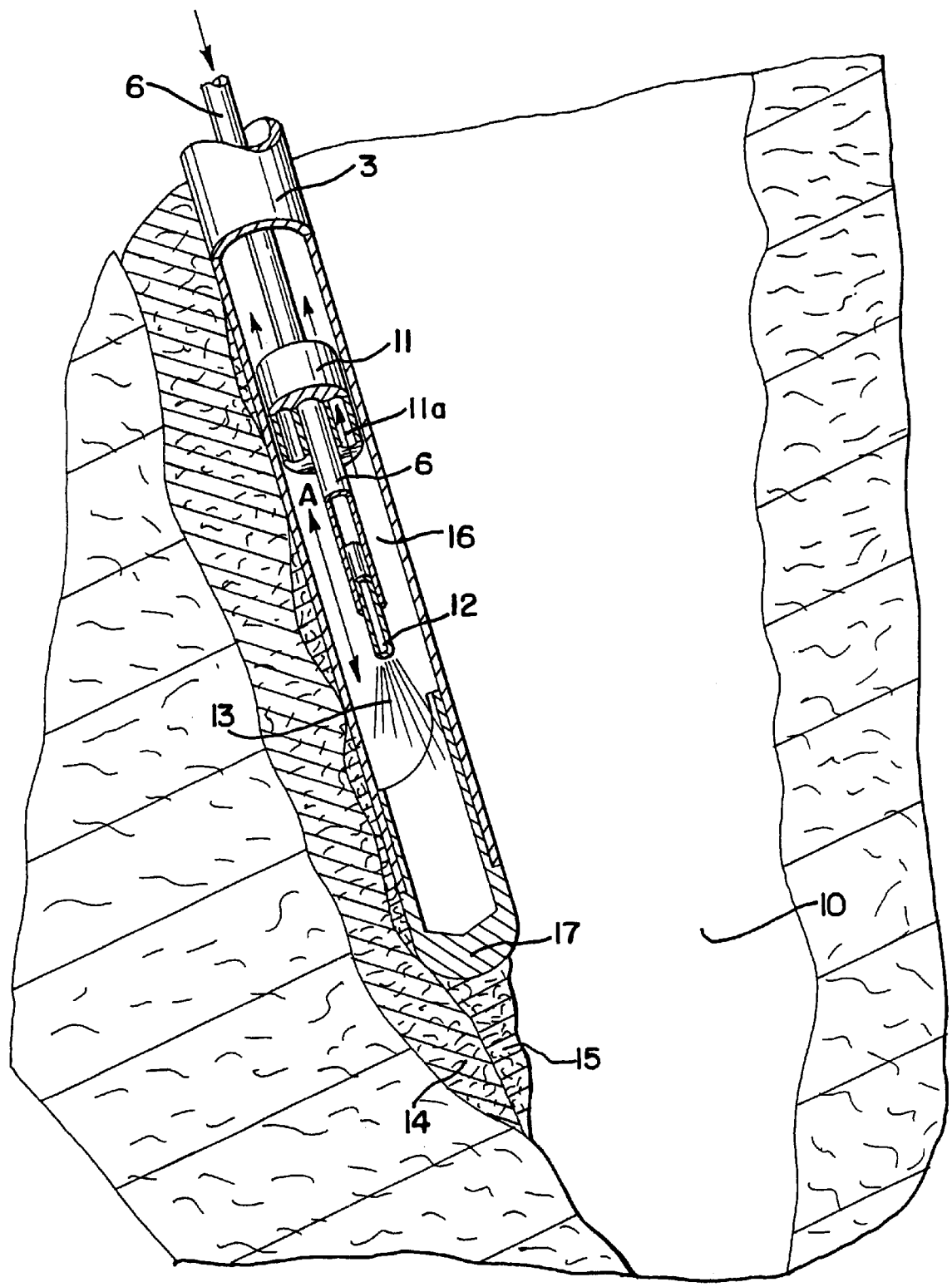
FIG. 2 illustrates in detail the cryoablation catheter according to the present invention placed within a human heart; and, FIG. 3 illustrates the entire cryoablation system in more detail.

FIG. 2 is a detailed and partly cross-sectional view of the distal end of the catheter 2 in a position for use. The internal body 6 opens out into the internal lumen 16 of the basic body 3 close to the distal end of the catheter. Through the internal body 6 a flow of $N_2O$ coolant is supplied, which is ejected via a nozzle 12, which preferably takes the form of a Joule-Thompson nozzle, so that a cold zone 13 is created. In the immediate proximity of this cold zone 13, at the nozzle 12 of the internal body 6, the coldness created on the outside of the basic body 3 is such that ice 15 is formed and the tissue 14 is ablated.

As has been described in connection with FIG. 1, the handle 5, which is connected with the internal body 6, is movable in relation to the connecting piece 4, which is connected with the basic body 3. In this manner the nozzle 12 at the distal end of the internal body 6 is moved in relation to the basic body 3. In the situation illustrated here, the basic body 3 on the other hand has in the meantime become stuck in the ice 15, and is consequently no longer movable. The internal body 6 and, in particular in the proximity of the nozzle 12 hereof, a sliding block 11 has been arranged around the internal body 6 close to the nozzle 12, which functions as a distancing body. The dimensions of the sliding block 11 correspond to those of the internal lumen 16 of the basic body 3, so that it can move freely up and down in the basic body 3 in the direction indicated by arrow "A," in which changes can be made in the position of the nozzle 12. The sliding block 11 also includes passageways 11a which extend through the sliding block. The sliding block 11 is provided with the passageways 11a to allow the coolant fluid to flow back from the cooling chamber.

All components of the catheter illustrated here have preferably been made of materials which do not shrink together due to expansion or contraction of the materials.

In the embodiment illustrated here, the basic body 3 has been closed off by means of a closure 17.

Figure 3:
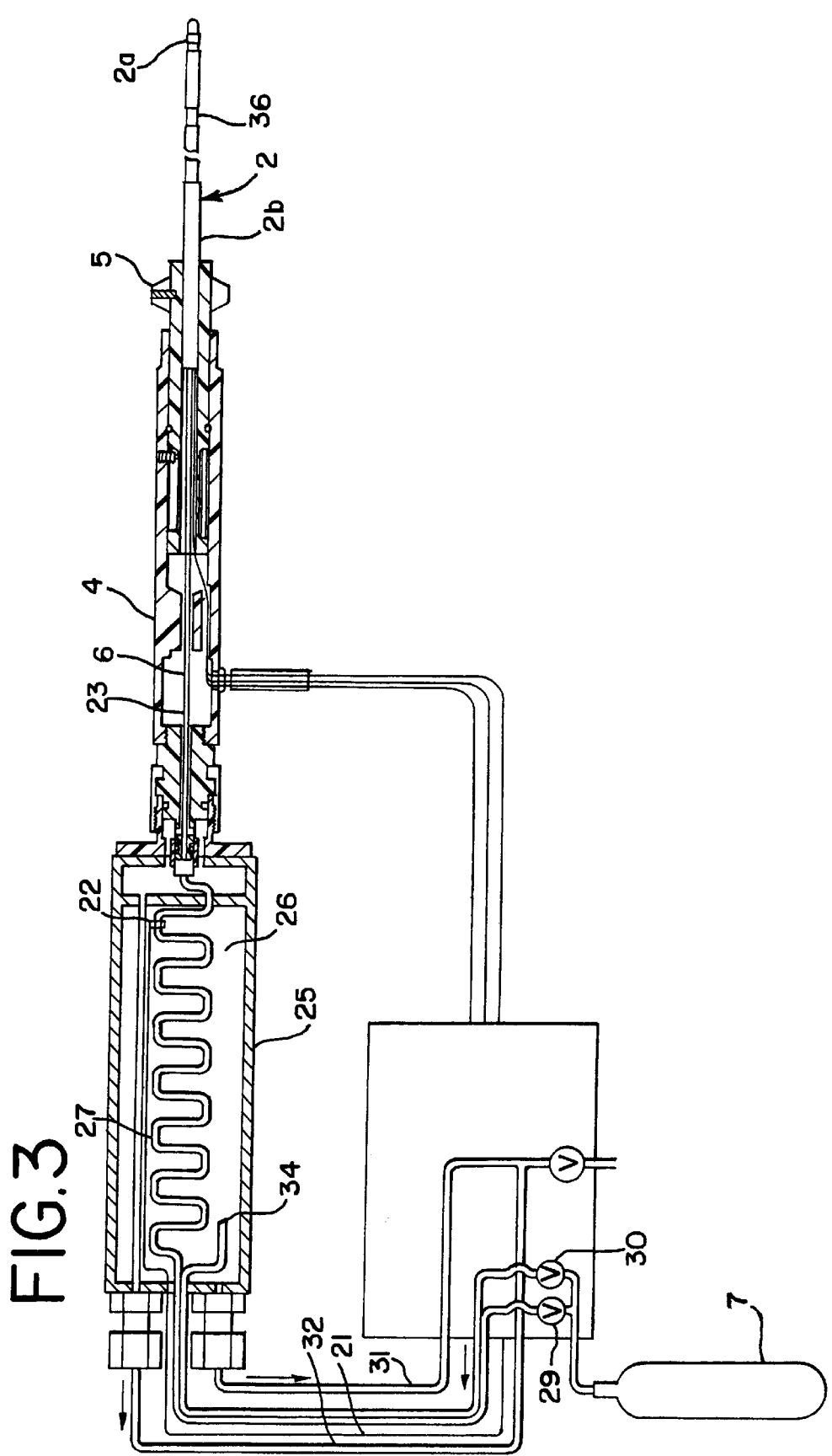

The catheter device illustrated in FIG. 3 shows a catheter tube according to the invention with a distal end 2a and a proximal end 2b. The proximal end carries a connecting piece 4, which includes a handle 5. A pressure line 23 extends from the proximal end of the catheter to the distal end. The pressure line 23 supplies high pressure refrigerant to the distal end of the catheter.

The expanded gaseous fluid flows, via the discharge channel formed by the internal lumen 16 in the catheter body and through the passageway 11a back to the proximal end of the catheter. The discharge channel of the catheter body is connected in a suitably sealed-off manner with the line 32 in the handle 5.

To achieve sufficient cooling effect in the tip of the catheter 2, the refrigerant is pre-cooled in the heat exchanger 25, before it is introduced into the catheter. The cooling means illustrated schematically in FIG. 3 comprises an insulated cooling chamber 26, through which a connecting pressure tube 27 extends in a helical pattern. The pressure line 23 is connected with this connection tube 27. The fluid under pressure is supplied to the connection tube 27 from a refrigerant source illustrated here as a gas cylinder 7. The required quantity is regulated by means of the adjustable valve 29.

Preceding the valve 29 a line branches off from the refrigerant line which, via a restriction 34, opens out into the cooling chamber 26. The quantity of fluid supplied to the cooling chamber 26 is regulated by the size and the dimensions of the restriction 34 and the control valve 30. On passing the restriction 34 the refrigerant expands in the chamber 26 and removes heat from the surroundings, that is to say from the refrigerant flowing through the connecting tube 27 which is cooled as a result. The expanded fluid is extracted from the chamber 26 through the line 31, so that a sufficient pressure difference is maintained across the restriction.

As shown in FIG. 3, a temperature sensor 22 has been arranged at the proximal end of the pressure line, which is connected via a signal line 21 with a temperature measuring 13 device. In this way it is possible to check the temperature of the refrigerant supplied to the proximal end of the pressure line 23. The control valve 30 may be regulated on the basis of the temperature measured. In another embodiment, the control valve 30 may be regulated by a control means on the basis of the temperature measured with the sensor 22.

A temperature sensor (not shown) may also be placed on the tip of the catheter 2. By means of the temperature sensor the temperature at the tip of the catheter 2 may be monitored. The value measured may also be used to adjust the adjustable valve 29. The adjustable valve 29 may also be regulated automatically in accordance with the temperature measured in the tip.

At the distal end the catheter may have been provided with a ring-shaped electrode which, by means of a signal line is also connected to a measuring device. Using the ring-shaped electrode 36, and in combination with the tip, measurements can be taken inside organs in order to establish the correct position for the ablation treatment.

The catheter device according to the invention is for instance used to ablate surface tissue inside the heart, when treating certain cardiac arrhythmias.

Because of the relatively high heat resistance coefficient of the material of which the pressure line 23 has been made, the pre-cooled fluid will at the most absorb only little heat from the surroundings. Inside the basic body 3 of the catheter 2 the pressure line 23 forming the internal body 6 extends through the central lumen. The expanded gas which is being removed from the tip flows through this lumen. This expanded gas has initially a very low temperature and is only heated to limited degree in the tip. The gas flowing through the lumen 16 forming the discharge channel consequently still has a low temperature, so that as a result none or only little heating of the refrigerant supplied under pressure will take place.

It should be noted that only a possible embodiment has been illustrated. Other embodiments are possible as well. The heat exchanger 25 for instance may be integrated into the handle 5. The pressure line 23 may in that case be surrounded along more or less its entire length by expanded fluid which is being discharged, so that the temperature of the pressure fluid may be controlled accurately. Alternatively, the nozzle configuration may be radially placed inside the distal end of the pressure tube, or in other possible configurations.

These modifications would be apparent to those having ordinary skill in the art to which this invention relates and are intended to be within the scope of the claims which follow.

That which is claimed is:

1. A cryoablation catheter system comprising a cryoablation catheter including:
    an outer tubular member having a proximal end and distal end and being capable of insertion into the vessels of the body;
    a sealing cap disposed at the distal end of the outer tubular member for forming a cooling chamber at a distal end of the catheter;
    an inner tubular member slidably disposed within the outer tubular member and having a proximal end and a distal end, the proximal end of the tubular member being adapted to receive a fluid which when expanded cools to an extremely low temperature;
    a fluid expansion nozzle disposed on the distal end of the inner tubular member;
    a control means coupled to the proximal end of the inner tubular member for moving the inner tubular member to thereby move the expansion nozzle longitudinally within the cooling chamber;
    a temperature sensor for sensing temperature of the fluid; and
    a device responsive to said temperature sensor for varying the temperature of said fluid.

2. A cryoablation catheter system as defined in claim 1, wherein the inner tubular member is disposed coaxially within the outer tubular member so as to define a passageway between the inner tubular member and the outer tubular member; and,
    a cylindrical support member is disposed between the inner tubular member and the outer tubular member, said support member having at least one passageway which extends through the support member to permit fluid to be returned through the passageway for removal from the catheter.

3. A cryoablation catheter system as defined in claim 2, wherein the control means takes the form of a control knob which is connected to the proximal end of the inner tubular member for movement of the inner tubular member longitudinally within the outer tubular member to thereby cause the position of the fluid expansion nozzle to change relative to the cooling chamber.

4. A cryoablation catheter system comprising a cryoablation catheter including:
    an outer tubular members having a proximal end and distal end and being capable of insertion into the vessels of the body;
    a sealing cap disposed at the distal end of the outer tubular member for forming a cooling chamber at a distal end of the catheter;
    an inner tubular member slidably disposed within the outer tubular member and having a proximal end and a distal end;
    a Joule-Thompson nozzle disposed on the distal end of the inner tubular member; and,
    a control means coupled to the proximal end of the inner tubular member for moving the inner tubular member to thereby move the Joule-Thompson nozzle longitudinally within the cooling chamber;
    a source of a high pressure gas coupled to the proximal end of the inner tubular member;
    a control valve for varying the pressure of the high pressure gas for varying the flow of gas to the Joule-Thompson nozzle;
    a temperature sensor for sensing temperature of the gas; and
    a device responsive to said temperature sensor for varying the temperature of said gas.

5. A cryoablation catheter system as defined in claim 4, wherein the inner tubular member is disposed coaxially within the outer tubular member so as to define a passageway between the inner tubular member and the outer tubular member; and,
    a cylindrical support member is disposed between the inner tubular member and the outer tubular member, said support member having at least one passageway which extends through the support member to permit fluid to be returned through the passageway for removal from the catheter.

6. A cryoablation catheter system as defined in claim 5, wherein the control means takes the form of a control knob which is connected to the proximal end of the inner tubular member for movement of the inner tubular member longitudinally within the outer tubular member to thereby cause the position of the fluid expansion nozzle to change relative to the cooling chamber.

7. A cryoablation catheter system comprising;
    an outer tubular member having a proximal end and a distal end and being capable of insertion into the vessels of the body;
    a sealing cap disposed at the distal end of the outer tubular member for forming a cooling chamber at a distal end of the catheter;
    an inner tubular member slidably disposed within the outer tubular member and having a proximal end and a distal end, the proximal end of the tubular member being adapted to receive a fluid which when expanded cools to an extremely low temperature;
    a Joule-Thompson nozzle disposed on the distal end of the inner tubular member;
    a control means coupled to the proximal end of the inner tubular member for moving the inner tubular member to thereby move the Joule-Thompson nozzle longitudinally within the cooling chamber;
    a temperature sensor for sensing temperature of the fluid; and
    a device responsive to said temperature sensor for varying the temperature of said fluid.

8. A cryoablation catheter system as defined in claim 7, wherein the inner tubular member is disposed coaxially within the outer tubular member so as to define a passageway between the inner tubular member and the outer tubular member; and, a cylindrical support member is disposed between the inner tubular member and the outer tubular member, said support member having at least one passageway which extends through the support member to permit fluid to be returned through the passageway for removal from the catheter.

* * * * *